(12) United States Patent
Merritt et al.

(10) Patent No.: US 6,187,798 B1
(45) Date of Patent: Feb. 13, 2001

(54) HETEROCYCLIC COMPOUNDS

(75) Inventors: Leander Merritt, Indianapolis, IN (US); Lone Jeppesen, Virum (DK); John S. Ward, Indianapolis, IN (US)

(73) Assignee: Eli Lilly and Company, Indianapolis, IN (US)

( * ) Notice: Under 35 U.S.C. 154(b), the term of this patent shall be extended for 0 days.

(21) Appl. No.: 09/171,795

(22) PCT Filed: Apr. 23, 1997

(86) PCT No.: PCT/US97/06698

§ 371 Date: Jun. 1, 1999

§ 102(e) Date: Jun. 1, 1999

(87) PCT Pub. No.: WO97/40043

PCT Pub. Date: Oct. 30, 1997

Related U.S. Application Data

(60) Provisional application No. 60/016,006, filed on Apr. 23, 1996.

(51) Int. Cl.[7] .................. A61K 31/425; C07D 417/02
(52) U.S. Cl. ............................ 514/362; 548/135
(58) Field of Search .............................. 548/135; 514/362

(56) References Cited

U.S. PATENT DOCUMENTS

| 5,605,908 | 2/1997 | Merritt et al. | 514/305 |
|---|---|---|---|
| 5,646,289 | 7/1997 | Alt et al. | 548/110 |

FOREIGN PATENT DOCUMENTS

| 0 709 381 A1 | 5/1996 | (EP) | 285/10 |
|---|---|---|---|

*Primary Examiner*—Robert Cerstl
(74) *Attorney, Agent, or Firm*—David M. Stemerick; Arleen Palmberg; Macharri R. Vorndran-Jone

(57) ABSTRACT

The present invention provides aza-bicyclo[2.2.1]heptane compounds which are useful for modulating a muscarinic receptor.

16 Claims, No Drawings

HETEROCYCLIC COMPOUNDS

This application is a 371 of PCT/US97/06698 filed Apr. 23, 1997 and claims benefit of provisional application Ser. No. 60/016,006 filed Apr. 23, 1996.

The present invention relates to therapeutically active azabicyclo[2.2.1]heptane compounds having surprising potency and favorable side effect profile. The novel compounds are useful as stimulants of the cognitive function of the forebrain and hippocampus of mammals.

Due to the generally improved health situation in the western world, elderly-related diseases are much more common now than in the past and are likely to be even more common in the future.

One of the elderly-related symptoms is a reduction of the cognitive functions. This symptom is especially pronounced in the pathophysiological disease known as Alzheimer's disease. This disease is combined with, and also most likely caused by, an up to 90% degeneration of the muscarinic cholinergic neurons in nucleus basalis, which is part of substantia innominata. These neurons project to the prefrontal cortex and hippocampus and have a general stimulatory effect on the cognitive functions of the forebrain as well as of hippocampus, namely learning, association, consolidation, and recognition.

It is a characteristic of Alzheimer's disease that although the cholinergic neurons degenerate, the postsynaptic muscarinic receptors in the forebrain and hippocampus still exist. Therefore, muscarinic cholinergic agonists are useful in the treatment of Alzheimer's disease, in halting its progression, and in improving the cognitive functions of elderly people.

Compounds active at a muscarinic cholinergic receptor are also useful analgesic agents and therefore are useful in the treatment of severely painful conditions.

Furthermore, muscarinic cholinergic receptor active compounds are useful in the treatment of glaucoma, psychosis, anxiety, mania, bipolar disorder, schizophrenia or schizophreniform conditions, depression, sleeping disorders, epilepsy, cerebral ischemia, and gastrointestinal motility disorders.

Therefore, new compounds having muscarinic cholinergic activity are desired. Some muscarinic cholinergic receptor active compounds are associated with side effects attributed to undesired modulation of the muscarinic cholinergic receptors, for example, such undesired modulation may cause excessive salivation and gastrointestinal upset. Thus, the most desired muscarinic cholinergic compounds shall have high potency and at the same time a favorable side effect profile, including a low incidence of excessive salivation.

The presently claimed compounds are surprisingly potent and provide a favorable side effect profile. Studies of the compounds claimed herein suggest that these compounds will be highly desired muscarinic receptor active compounds which can be particularly useful pharmaceutically active compounds.

This invention provides compounds of the formula I:

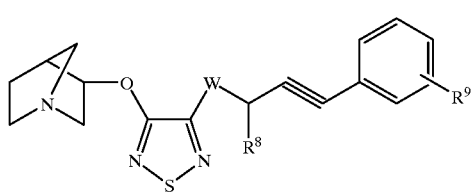

W is S or O;

$R^8$ is selected from the group consisting of hydrogen and $C_1$–$C_4$ alkyl;

$R^9$ is selected from the group consisting of halogen, $C_{1-4}$-alkyl, $C_{1-4}$-alkoxy, —CN, —OCF$_3$, —CF$_3$, —CONH$_2$ and —CSNH$_2$; and pharmaceutically acceptable salts and solvates thereof.

Preferred compounds are those wherein $R^9$ is chloro and in the para position on the phenyl group.

The present invention further provides a formulation comprising a compound of Formula I and one or more carriers or diluents therefor.

Additionally, the present invention provides a method for treating a condition which is mediated by a muscarinic receptor comprising administering an effective amount of a compound of Formula I to a mammal in need of such treatment.

It is to be understood that the invention extends to each of the stereoisomeric forms of the compounds of the present invention as well as the pure diastereomeric, pure enatiomeric, and racemic forms of the compounds of this invention.

As used herein the term "treating" includes prophylaxis of a physical and/or mental condition or amelioration or elimination of the developed physical and/or mental condition once it has been established or alleviation of the characteristic symptoms of such condition.

As used herein the phrase "interacting with a muscarinic cholinergic receptor" shall include compounds which block muscarinic cholinergic receptors or modulate such receptors. The phrase shall include the effect observed when compounds act as agonists, partial agonists and/or antagonists at a muscarinic cholinergic receptor.

As used herein the phrase "a condition which is mediated by a muscarinic receptor" shall refer to a condition which can be treated by administering a compound which acts as a muscarinic receptor antagonist, agonist, or mixed agonist at a muscarinic receptor. Such conditions shall include, but are not limited to, Alzheimer's disease, severely painful conditions, glaucoma, psychosis, anxiety, mania, bipolar disorder, schizophrenia or schizophreniform conditions, depression, sleeping disorders, epilepsy, cerebral ischemia, and gastrointestinal motility disorders.

As used herein, the term "halogen" means Cl, Br, F, and I. Especially preferred halogens include Cl, Br, and I. A particularly preferred halogen is Cl.

As used herein the phrase "one or more selected from" shall more preferredly refer to from 1–3 substituents. The term shall further preferredly refer to from 1–2 substituents.

The terms "$C_n$'–$C_4$ alkyl" wherein n' can be 1 or 2, as used herein, represent a branched or linear alkyl group having from one to 4 carbon atoms. Typical $C_1$–$C_4$ alkyl groups include, but are not limited to, methyl, ethyl, n-propyl, iso-propyl, butyl, iso-butyl, sec-butyl, tert-butyl and the like.

The term "$C_1$–$C_4$ alkoxy" refers to a carboxy group such as, but not limited to, methoxy, ethoxy, propoxy, butoxy, and the like. The alkoxy substituent is attatched to the parent molecule through the oxygen atom of the alkoxy group.

As used herein the term "h$^+$" is an alkoxide metal. As used herein, the term "alkoxide metal" means a metal suitable for alkoxide formation. Such alkoxide metals include, but are not limited to, Li$^+$, K$^+$, Na$^+$, Cs$^+$, and Ca$^{++}$. Especially preferred alkoxide metals include Li$^+$, K$^+$, and Na$^+$.

As used herein, the phrase "5 or 6 membered heterocyclic group" or "5 membered heterocycle" means a group containing from one to four N, O or S atom(s) or a combination thereof, which heterocyclic group is optionally substituted at carbon or nitrogen atom(s) with $C_{1-6}$-alkyl, -$CF_3$, phenyl, benzyl or thienyl, or a carbon atom in the heterocyclic group together with an oxygen atom form a carbonyl group, or which heterocyclic group is optionally fused with a phenyl group. The phrase "5 or 6 membered heterocyclic group" includes, but is not limited to, 5-membered heterocycles having one hetero atom (e.g. thiophenes, pyrroles, furans); 5-membered heterocycles having two heteroatoms in 1,2 or 1,3 positions (e.g. oxazoles, pyrazoles, imidazoles, thiazoles, purines); 5-membered heterocycles having three heteroatoms (e.g. triazoles, thiadiazoles); 5-membered heterocycles having 3-heteroatoms; 6-membered heterocycles with one heteroatom (e.g. pyridine, quinoline, isoquinoline, phenanthrine, 5,6-cycloheptenopyridine); 6-membered heterocycles with two heteroatoms (e.g. pyridazines, cinnolines, phthalazines, pyrazines, pyrimidines, quinazolines); 6-membered heterocycles with three heteroatoms (e.g. 1,3,5-triazine); and 6-member heterocycles with four heteroatoms. Particularly preferred are thiophenes, pyridines, and furans.

Examples of pharmaceutically acceptable salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salts, and include the pharmaceutically acceptable salts listed in *Journal of Pharmaceutical Science*, 66, 2 (1977) which are known to the skilled artisan. The compounds of this invention may form solvates with standard low molecular weight solvents using methods known to the skilled artisan.

As described in the following Schemes, the following substituents have the meaning as follows unless otherwise indicated:

W is oxygen or sulphur;

R is selected from the group consisting of hydrogen, amino, halogen, $NHR^6$, $NR^6R^7$, $R^4$, —$OR4$, —$SR^4$, —$SOR^4$, —$SO_2R^4$, $C_{3-10}$-cycloalkyl, $C_{4-12}$- (cycloalkylalkyl), —Z—$C_{3-10}$-cycloalkyl and —Z—$C_{4-12}$- (cycloalkylalkyl);

$R^4$ is selected from the group consisting of $C_{1-15}$-alkyl, $C_{2-15}$-alkenyl and $C_{2-15}$-alkynyl, each of which is optionally substituted with one or more independently selected from the group consisting of halogen(s), —$CF_3$, —CN, Y, phenyl and phenoxy wherein phenyl or phenoxy is optionally substituted with one or more independently selected from the group consisting of halogen, —CN, $C_{1-4}$-alkyl, $C_{1-4}$-alkoxy, —$OCF_3$, —$CF_3$, —$CONH_2$ and —$CSNH_2$; or R is phenyl or benzyloxycarbonyl, each of which is optionally substituted with one or more independently selected from the group consisting of halogen, —CN, $C_{1-4}$-alkyl, $C_{1-4}$-alkoxy, —$OCF_3$, —$CF_3$, —$CONH_2$ and —$CSNH_2$; or R is selected from the group consisting of —$OR^5Y$, —$SR^5Y$, $OR^5$-Z—Y, —$SR^5ZY$, —O—$R^5$-Z—$R^4$ and —S—$R^5$-Z—$R^4$;

Z is oxygen or sulphur, $R^5$ is $C_{1-15}$-alkyl, $C_{2-15}$-alkenyl, and $C_{2-15}$-alkynyl;

Y is a 5 or 6 membered heterocyclic group;

G is selected from one of the following azacyclic or azabicyclic ring systems:

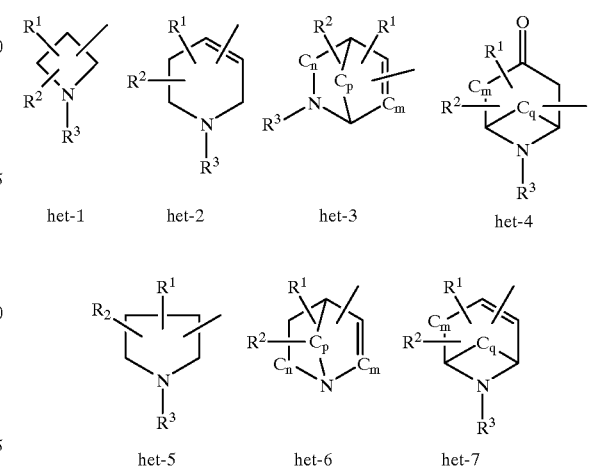

het-1  het-2  het-3  het-4 het-5  het-6  het-7 or G is optionally substituted $C_3$–$C_8$ cycloalkyl wherein the cycloalkyl substituents are selected from $R^1$ and $R^2$; or optionally substituted $C_{1-6}$-alkyl wherein the substitution is —$NR^6R^7$;

$R^6$ and $R^7$ independently are selected from the group consisting of hydrogen and $C_{1-6}$-alkyl; or $R^6$ and $R^7$ together with the nitrogen atom optionally form a 4- to 6-member ring;

$R^1$ and $R^2$ independently are selected from the group consisting of hydrogen, $C_{1-15}$-alkyl, $C_{2-5}$-alkenyl, $C_{2-5}$-alkynyl, $C_{1-10}$alkoxy, and $C_{1-5}$-alkyl substituted with one or more independently selected from the group consisting of —OH, —$COR^{6'}$, $CH_2$-OH, halogen, —$NH_2$, carboxy,

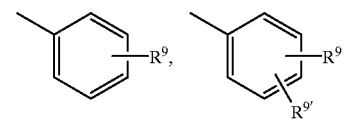

and phenyl;

$R^{6'}$ is hydrogen, $C_{1-6}$-alkyl;

$R^3$ is selected from the group consisting of hydrogen, $C_{1-5}$-alkyl, $C_{2-5}$-alkenyl and $C_{2-5}$-alkynyl;

n is 0, 1 or 2;

m is 0, 1 or 2;

p is 0, 1 or 2;

q is 1 or 2;

r is 0, 1 or 2;

——— is a single or double bond.

The compounds of this invention can be prepared using the chemical processes illustrated in Scheme I' and Scheme I. The starting materials for the illustrated process are commercially available or may be prepared using methods known to the skilled artisan.

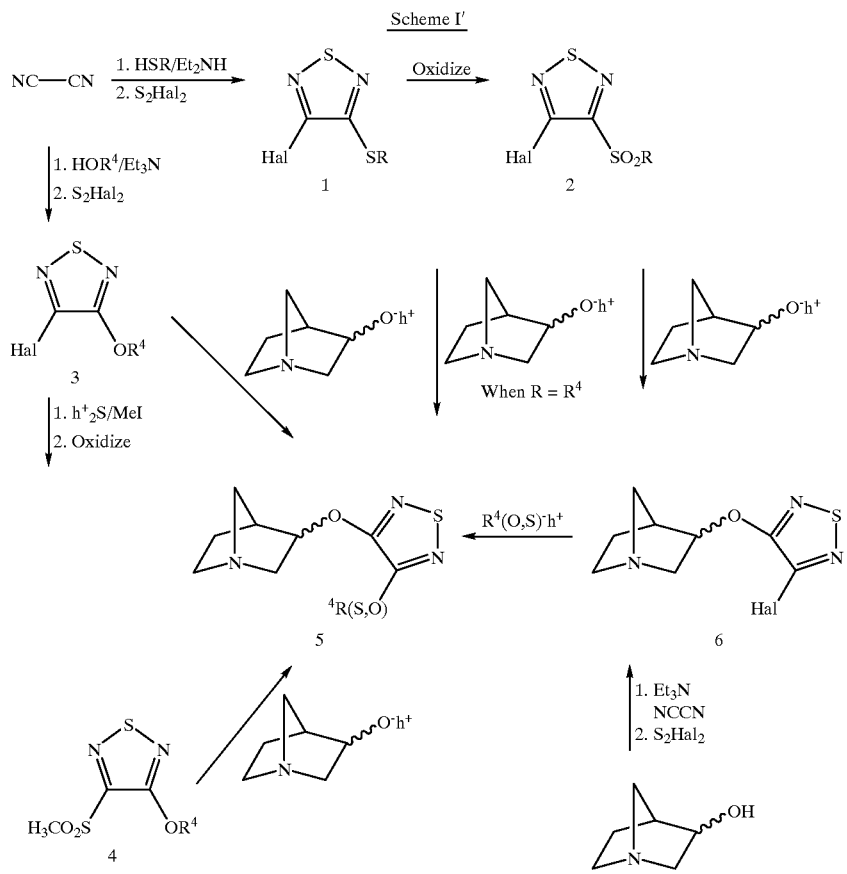
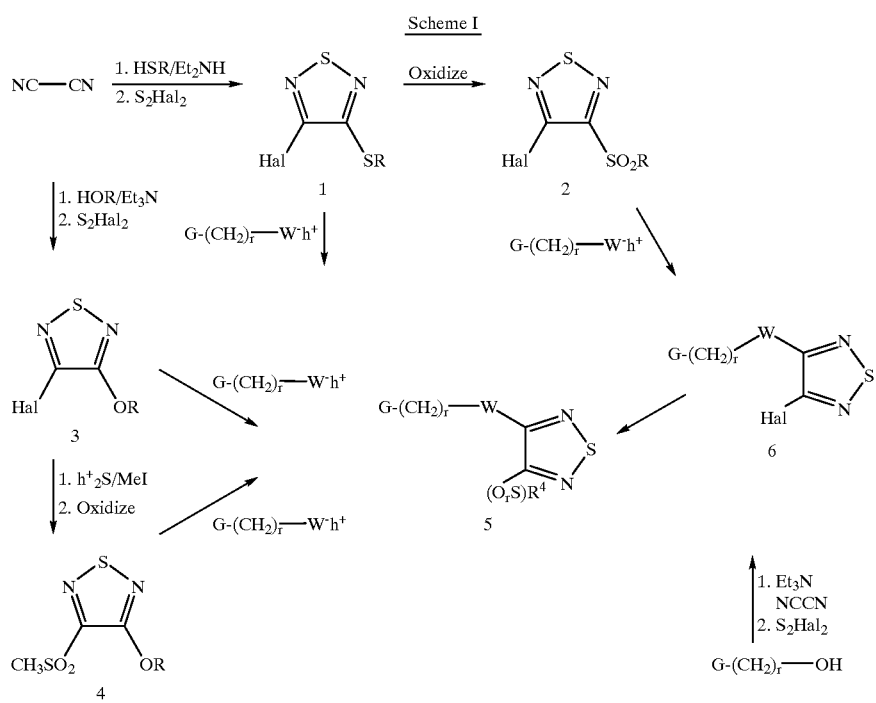

As used in Scheme I, R, h+, and G are as defined supra. As used in Scheme I, the term "Hal" refers to Cl and Br. Preferred oxidizing agents for the process of Scheme I include oxone and sodium periodate. Oxone is an especially preferred oxidizing agent for the process of Scheme I. Compounds of Formula 3, as illustrated in Scheme I wherein the OR group is replaced by an $R^4$ group, can be prepared using methods well known in the art. See for example, U.S. Patent Number 5,043,345.

Further, compounds of Formula I may be prepared using the process illustrated in the following Schemes II and II'

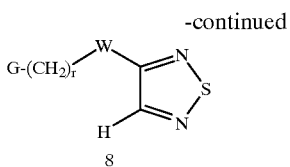

As used in Scheme III, Hal, W, r, and G are as defined supra. As used in Scheme III, $R^{22}$ and $R^{23}$ are independently selected from the group consisting of hydrogen, $R^6$ and $R^7$.

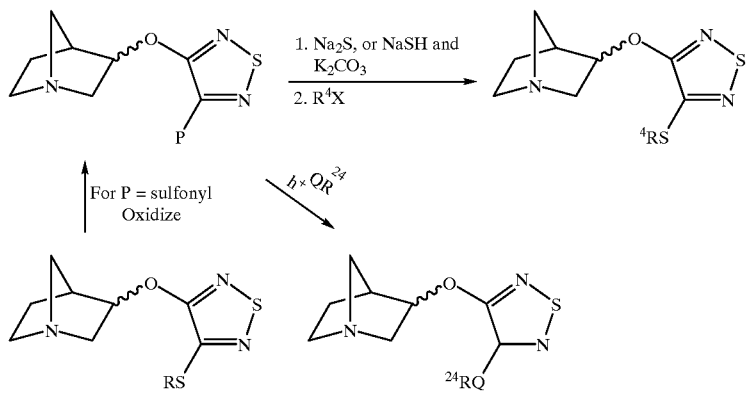

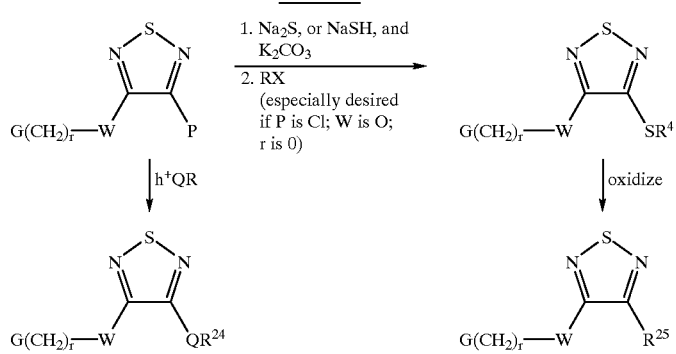

As used in Scheme II and II', P may be hal or $SO_2R^9$; Q may be N, O or S; $R^{24}$ is selected from the group consisting of hydrogen, $R^4$, $R^5$, $R^6$, and $R^7$; $R^{25}$ is selected from the group consisting of $SOR^4$ and $SO_2R^4$; all other meanings are as defined supra.

Additional compounds of Formula I may be prepared using the process illustrated by Scheme III.

Certain intermediates of the present invention may be prepared using the process illustrated in Scheme IV.

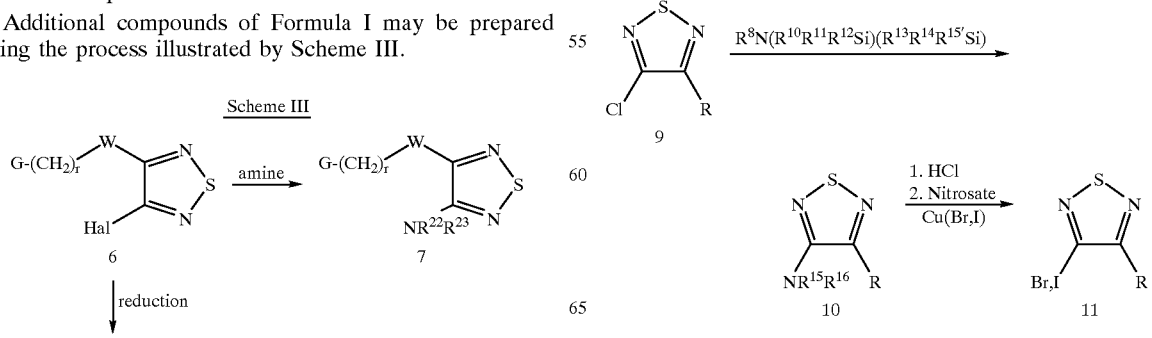

As used in Scheme IV, $R^8$, Si, $R^{10}$, $R^{11}$, $R^{12}$, $R^{13}$, $R^{14}$, $R^{15'}$, $R^{15}$ and $R^{16}$ are as defined supra. For example, $R^8N[(R^{10}R^{11}R^{12}Si)(R^{13}R^{14}R^{15'}Si)]$ may be, but is not limited to lithium bis(tri-2-propylsilyl)amide, sodium bis(trimethylsilyl)amide, potassium bis(trimethylsilyl)amide, lithium bis(tri-2-propylsilyl)amide, sodium bis(ethyldimethylsilyl)amide, potassium bis(1-propylethylmethylsilyl)amide, lithium bis(tri-phenylsilyl)amide, sodium bis(tri-phenylmethylsilyl)amide, potassium bis(2-butyl-2-propylmethylsilyl)amide, lithium (tri-2-propylsilyi)(2-butyldiethylsilyl) amide, sodium (trimethylsilyl)(triphenylsilyl)amide, potassium (dimethyl phenylsilyl)(ethyldimethylsilyl)amide, and the like. Most preferably, $R^{15}$ and $R^{16}$ are each hydrogen when the process of Scheme III is used for preparing a compound of 11 from a compound of 10. The intermediate 10 may be nitrosated using standard nitrosating procedures. A preferred nitrosating agent is isoamyl nitrite; however, other known nitrosating agents are appropriate. As used in Scheme III, the term "Cu(Br,I)" refers to copper (I) bromide, copper (II) bromide, or copper (I) iodide. The artisan will recognize that the copper (I) bromide, copper (II) bromide, or copper (I) iodide reagent shall determine the substitution on the product of the process illustrated in Scheme III.

Certain compounds of this invention may more preferably be prepared by a process using a hydroxyalkylamine (G—OH) wherein G has the meaning defined supra. in the presence of a phosphorus(III) compound and a diester of azodicarboxylate to give the 1,2,5-thiadiazoyloxyalkylamine as illustrated by Scheme V and V'.

Scheme V'

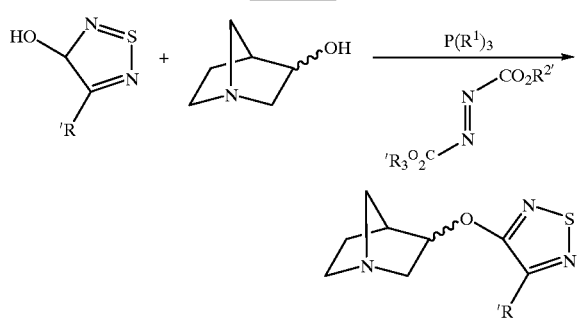

Scheme V

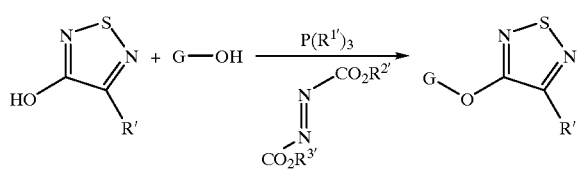

The G group is 2-aza-bicyclo[2.2.1]heptane. The R'is selected from the group consisting of —$OR^4$ and —$SR^4$ $R^4$ is selected from the group consisting of $C_{1-15}$-alkyl, $C_{2-15}$-alkenyl, $C_{2-15}$-alkynyl and 5-membered heterocycle, each of which is optionally substituted with one or more independently selected from the group consisting of halogen (s), —$CF_3$, —CN, Y, phenyl and phenoxy wherein phenyl or phenoxy is optionally substituted with one or more independently selected from the group consisting of halogen, —CN, $C_{1-4}$-alkyl, $C_{1-4}$-alkoxy, —$OCF_3$, or —$CF_3$; or R' is phenyl or benzyloxycarbonyl, each of which is optionally substituted with one or more independently selected from the group consisting of halogen, —CN, $C_{1-4}$-alkyl, $C_{1-4}$-alkoxy, —$OCF_3$, and —$CF_3$; or R' selected from the group consisting of —$OR^5y$, —$SR^5Y$, $OR^5$-Z—Y, —$SR^5ZY$, —O—$R^5$-Z—$R^4$ and —S—$R^5$-Z—$R^4$;

Z is oxygen or sulphur;

$R^5$ is selected from the group consisting of $C_{1-15}$-alkyl, $C_{2-15}$-alkenyl, and $C_{2-15}$-alkynyl;

Y is a 5-membered heterocyclic group;

$R^{1'}$is selected from the group consisting of phenyl, $C_{1-15}$-alkyl, $C_{2-5}$-alkenyl, $C_{2-5}$-alkynyl and $(NR^{2'})_3$;

$R^{2'}$and $R^{3'}$are independently selected from the group consisting of hydrogen, $C_{1-15}$-alkyl, $C_{2-5}$-alkenyl, $C_{2-5}$-alkynyl, and $C_{1-5}$-alkyl substituted with one or more selected from the group consisting of halogen and phenyl;

W is oxygen or sulphur;

$R^6$, and $R^7$ independently are $C_{1-6}$-alkyl; or $R^6$ and $R^7$ together with the nitrogen atom optionally form a 4- to 6-member ring;

$R^1$ and $R^2$ are independently selected from hydrogen, $C_{1-15}$-alkyl, $C_{2-5}$-alkenyl, $C_{2-5}$-alkynyl, $C_{1-10}$-alkoxy, and $C_{1-5}$-alkyl substituted with one or more independently selected from the group consisting of —$COR^{6'}$, halogen, and phenyl;

$R^{6'}$is hydrogen or $C_1$–$C_3$ alkyl;

$R^3$ is selected from the group consisting of $C_{1-5}$-alkyl, $C_{2-5}$-alkenyl and $C_{2-5}$-alkynyl;

10 n is 0, 1 or 2;

m is 0, 1 or 2;

p is 0, 1 or 2;

q is 1 or 2;

r is 0, 1 or 2;

......... is a single or double bond.

Preferred $R^{1'}$ groups include phenyl, $C_{1-15}$-alkyl, and $(NR^{2'})_3$. The process of Scheme IV is particularly advantageous because the process provides a method for inverting the stereochemistry at the carbon bearing the hydroxyl group in G.

Another new process illustrated by Schemes VI and VI', involves the sequential reaction of 3,4-dihydroxy-1,2,5-thiadiazole with G—OH wherein G is defined as defined supra. in the presence of a phosphorous(III) compounds and a diester of azodicarboxylate to give an unisolated hydroxy-1,2,5-thiadiazole ether I″ followed by reaction of I″ with $R^4OH$ where $R^4$ is defined as supra. with phosphorous(III) compounds and a diester of azodicarboxylate to give the diethers of 3,4-dihydroxy-1,2,5-thiadiazole which are useful as muscarinic agonists and antagonists. (See, *Org. Prep. & Procedures* 1969, 1, 255–258) The substituents illustrated in Scheme VI are as defined supra.

Scheme VI'

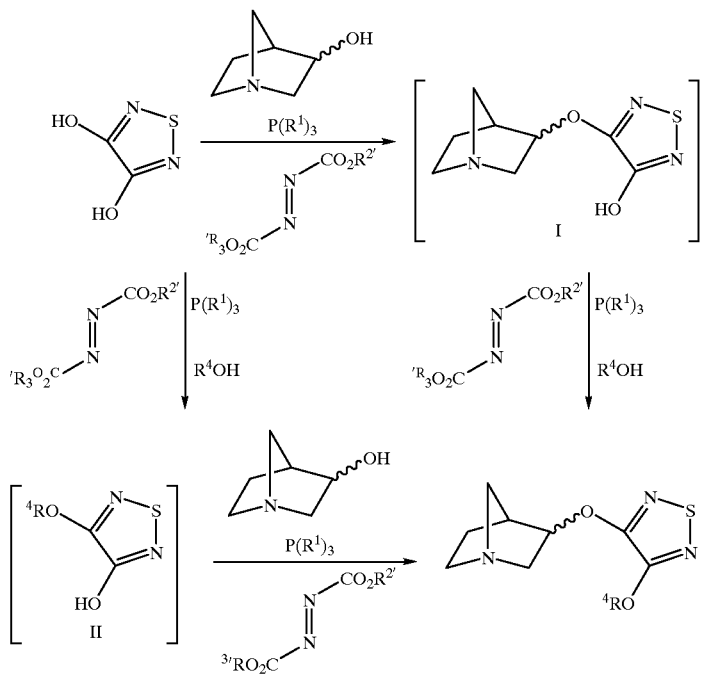

Scheme VI

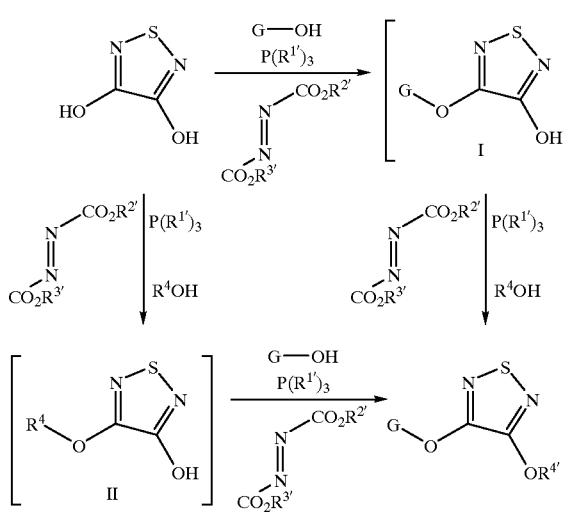

Alternatively, the order of addition of the alcohols may be reversed as shown above to give unisolated hydroxy-1,2,5-thiadiazole ether II which is subsequently converted to the same final muscarinic active compound.

The process illustrated by Scheme VII encompasses the reaction of a phenol or hydroxyheteroaryl compound with compound III in the presence of a phosphorus(III) compound and a diester of azodicarboxylate to give compound IV.

Scheme VII

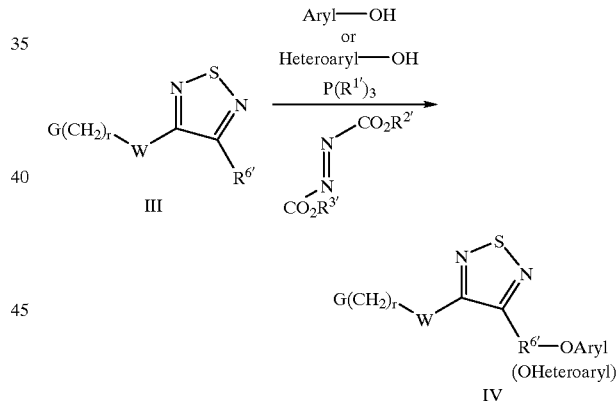

In compound III, $G(CH_2)_rW$ is 2-Aza-bicyclo[2.2.1]heptane and $R^{6'}$ is selected from the group consisting of $R^7$, —$OR^7$, —$SR^7$, —$SOR^7$, —$SO_2R^7$, $C_{3-10}$-cycloalkyl, $C_{4-12}$-(cycloalkylalkyl), —Z—$C_{3-10}$-cycloalkyl and —Z—$C_{4-12}$-(cycloalkylalkyl);

$R^7$ is $C_{1-5}$-alkyl, $C_{2-15}$-alkenyl, $C_{2-15}$-alkynyl, each of which is optionally substituted with one or more independently selected from the group consisting of halogen(s), —$CF_3$, —CN, Y, phenyl and phenoxy; wherein phenyl or phenoxy is optionally substituted with one or more selected from the group consisting of halogen, —CN, $C_{1-4}$-alkyl, $C_{1-4}$-alkoxy, —$OCF_3$, and —$CF_3$;

provided that at least one alkyl atom of $R^{6'}$ is substituted with a hydroxyl group or $R^{6'}$ is a substituent selected from the group consisting of —$OR^8Y$, —$SR^8Y$, $OR^8$-Z—Y, —$SR^8ZY$, —O—$R^8$-Z—$R^7$ and —S—$R^8$-Z—$R^7$ wherein each —$OR^8Y$, —$SR^8Y$, $OR^8$-Z—Y, —$SR^8ZY$, —O—$R^8$-Z—$R^7$ and —S—$R^8$-Z—$R^7$ is substituted with a alkylhydroxyl;

Y is a 5 or 6 membered heterocyclic group;
Z is oxygen or sulphur;
$R^8$ is $C_{1-5}$-alkyl, $C_{2-15}$-alkenyl, $C_{2-15}$-alkynyl;
aryl and heteroaryl is optionally substituted with one or more independently selected from the group consisting of halogen, —CN, $C_{1-4}$-alkyl, $C_{1-4}$-alkoxy, $C_{1-4}$-alkylthio, $C_{1-4}$-alkylsulfone, $C_{1-4}$-alkylsulfoxide, —$OCF_3$, $NO_2$, $N(R^7)_2$, and —$CF_3$; heteroaryl group is a 5 or 6 membered heterocycle containing one to four N, O, or S atoms or a combination thereof.

Another process of this invention, illustrated by Scheme VIII, is the synthesis of 3-hydroxy-4-alkylthio-1,2,5-thiadiazoles by treating 3-halo-4-alkylthio-1,2,5-thiadiazoles with aqueous alkaline metal hydroxides in the presence or absence of a dipolar aprotic solvent. In this scheme, Hal has the meanings defined supra. and M is an alkali metal, W is O or S.

Scheme VIII

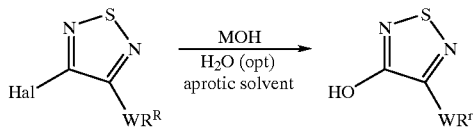

$R^R$ is hydrogen, $R^4$, $C_{3-10}$-cycloalkyl, $C_{4-12}$-(cycloalkylalkyl), $R^4$-Z—$C_{3-10}$-cycloalkyl and $R^4$-Z—$C_{4-12}$-(cycloalkylalkyl); W is oxygen or sulfur;
$R^4$ is selected from the group consisting of $C_{1-15}$-alkyl, $C_{2-15}$-alkenyl, and $C_{2-15}$-alkynyl, each of which is optionally substituted with one or more independently selected from the group consisting of halogen(s), —$CF_3$, Y, phenyl and phenoxy; wherein phenyl or phenoxy is optionally substituted with one or more selected from the group consisting of halogen, $C_{1-4}$-alkyl, $C_{1-4}$-alkoxy, and —$CF_3$; or $R^R$ is phenyl or benzyloxycarbonyl, each of which is optionally substituted with one or more selected from the group consisting of halogen, $C_{1-4}$-alkyl, $C_{1-4}$-alkoxy, and —$CF_3$; or
$R^R$ is $R^4$-$OR^5Y$, $R^4$-$SR^5Y$, $R^4$-$OR^5$-Z—Y, $R^4$-$SR^5ZY$, $R^4$-O—$R^5$-Z—$R^4$ or $R^4$-S—$R^5$-Z—;
Z is oxygen or sulphur;
$R^5$ is selected from the group consisting of $C_{1-15}$-alkyl, $C_{2-15}$-alkenyl, and $C_{2-15}$-alkynyl;
Y is a 5 or 6 membered heterocyclic group; and
$R^6$, and $R^7$ independently are hydrogen, $C_{1-6}$-alkyl, or $R^6$ and $R^7$ together with the nitrogen atom optionally form a 4- to 6-member ring;
$R^1$ and $R^2$ independently are hydrogen, $C_{1-15}$-alkyl, $C_{2-5}$-alkenyl, $C_{2-5}$-alkynyl, $C_{1-10}$-alkoxy, $C_{1-5}$-alkyl substituted with —OH, —$COR^{6'}$, $CH_2$-OH, halogen, —$NH_2$, carboxy, or phenyl;
$R^{6'}$ is hydrogen or $C_1$-$C_3$ alkyl;
W is O or S;
Hal is selected from Cl, Br, F, I, and if W is O then Hal may be $SO_2R^{4'}$;
$R^{4'}$ is $C_1$-$C_3$ alkyl or phenyl.

The compounds (11) are useful intermediates for the preparation of 1,2,5-thiadiazole compounds. The artisan will recognize that the intermediates 11 are useful for preparing 1,2,5-thiadiazole compounds as illustrated by the processes of Schemes I, II, and III.

When the G substituent contains a secondary nitrogen protected by a protecting group, the protecting group may be removed using standard methods known to the skilled artisan. An especially preferred protecting group is carbamate. One particularly useful reference concerning protecting groups is Greene, *Protecting Groups in Organic Synthesis*, (John Wiley & Sons, New York, 1981).

The concentration of the reactants is not critical. The art worker can alter the concentration of the reactants to achieve the desired rate of reaction and product yield.

The length of time for carrying out the processes described are not critical. As is always the case in chemistry, the rate of the reaction depends on a variety of factors, such as the temperature and the exact compound which is to be prepared. The course of the reaction may be followed using methods such as thin layer chromatography (TLC), high performance liquid chromatography (HPLC), gas chromatography (GC) and nuclear magnetic resonance spectroscopy (NMR) to detect the degree of completion of the reaction. The operator may obtain maximum yields using the process by extending the reaction time. Alternatively, the operator may wish to obtain maximum throughput by cutting off the reaction at the point at which it reaches an economical degree of completion.

When the product of a step in the following process is an oil, it may be isolated by standard methods. Such methods include distillation, flash chromatography, HPLC and the like.

As used herein the term "malfunctioning of the muscarinic cholinergic system" shall have the meaning accepted by the skilled artisan. For example the term shall refer to, but is not in any way limited to, conditions such as glaucoma, psychosis, schizophrenia or schizophreniform conditions, depression, sleeping disorders, epilepsy, and gastrointestinal motility disorders. Other such conditions include Alzheimer's Disease and incontinence.

The pharmacological properties of the compounds of the invention can be illustrated by determining their capability to inhibit the specific binding of $^3$H-Oxotremorine-M ($^3$H-Oxo). Birdsdall N. J. M., Hulme E. C., and Burgen A. S. V. (1980). "The Character of Muscarinic Receptors in Different Regions of the Rat Brain". Proc. Roy. Soc. London (Series B) 207,1.

$^3$H-oxo labels muscarinic receptor in the CNS (with a preference for agonist domains of the receptors). Three different sites are labeled by $^3$H-Oxo. These sites have affinity of 1.8, 20 and 3000 nM, respectively. Using the present experimental conditions only the high and medium affinity sites are determined.

The inhibitory effects of compounds on $^3$H-oxo binding reflects the affinity for muscarinic acetylcholine receptors.

All preparations are performed at 0–4° C. unless otherwise indicated. Fresh cortex (0.1–1 g) from male Wistar rats (150–250 g) is homogenized for 5–10 seconds in 10 mL 20 nM Hepes pH: 7.4, with an Ultra-Turrax homogenizer. The homogenizer is rinsed with 10 mL of buffer and the combined suspension centrifuged for 15 min. at 40,000×g. The pellet is washed three times with buffer. In each step the pellet is homogenized as before in 2×10 mL of buffer and centrifuged for 10 min. at 40,000×g.

The final pellet is homogenized in 20 mM Hepes pH: 7.4 (100 mL per g of original tissue) and used for binding assay. Aliquots of 0.5 mL is added 25 μL of test solution and 25 μL of $^3$H-Oxotremorine (1.0 nM, final concentration) mixed and incubated for 30 min. at 25° C. Non-specific binding is determined in triplicate using arecoline (1 μg/mL, final concentration) as the test substance. After incubation samples are added 5 mL of ice-cold buffer and poured directly onto Whatman GF/C glass fiber filters under suction and immediately washed 2 times with 5 mL of ice-cold buffer. The amount of radioactivity on the filters are determined by conventional liquid scintillation counting. Specific binding is total binding minus non specific binding.

Test substances are dissolved in 10 mL water (if necessary heated on a steam-bath for less than 5 min.) at a concentration of 2.2 mg/mL. 25–75% inhibition of specific binding must be obtained before calculation of $IC_{50}$. The test value will be given as $IC_{50}$ (the concentration (nM) of the test substance which inhibits the specific binding of $^3$H-oxo by 50%).

IC50=(applied test substance concentration)×$(C_x/C_o-C_x)$nM where CO is specific binding in control assays and $C_x$ is the specific binding in the test assay. (The calculations assume normal mass-action kinetics).

Furthermore the pharmacological properties of the compounds of the invention can also be illustrated by determining their capability to inhibit $^3$HPRZ (pirenzepine, [N-methyl-$^3$H]) binding to rat cerebral cortex membranes.

Pirenzepine binds selectively to subtype of muscarinic receptors. Historically the type is named the $M_1$ site, whereas pirenzepine sensitive site would be more appropriate. Although selective for $M_1$-sites pirenzepine also interact with $M_2$-sites.

All preparations are performed at 0–4° C. unless otherwise indicated. Fresh cortex (0.1–1 9) from male Wistar rats (150–200 g) is homogenized for 5–10 s in 10 mL 20 mM Hepes pH: 7.4, with an Ultra-Turrax homogenizer. The homogenizer is rinsed with 2×10 mL of buffer and the combined suspension centrifuged for 15 min. at 40,000×g. The pellet is washed three times with buffer. In each step the pellet is homogenized as before in 3×10 mL of buffer and centrifuged for 10 min. at 40,000×g.

The final pellet is homogenized in 20 mM Hepes pH: 7.4 (100 mL per g of original tissue) and used for binding assay. Aliquots of 0.5 mL is added 20 μl of test solution and 25 μL of $^3$HPRZ (1.0 nM, final conc.), mixed and incubated for 60 min. at 20° C. Non-specific binding is determined in triplicate using atropine (1 μg/mL, final conc.) as the test substance. After incubation samples are added 5 mL of ice-cold buffer and poured directly onto Whatman GF/C glass fiber filters under suction and immediately washed 2 times with 5 mL of ice-cold buffer. The amount of radioactivity on the filters are determined by conventional liquid scintillation counting. Specific binding is total binding minus non-specific binding.

Test substances are dissolved in 10 mL water, at a concentration of 0.22 mg/mL. 25–75% inhibition of specific binding must be obtained before calculation of $IC_{50}$.

The test value will be given as $IC_{50}$ (the concentration (nM) of the test substance which inhibits the specific binding of $^3$HPRZ by 50%).

$IC_{50}$=(applied test substance concentration)×$(C_x/C_o-C_x)$nM where $C_o$ is specific binding in control assays and $C_x$ is the specific binding in the test assay. (The calculations assume normal mass-action kinetics).

Additionally, the pharmacological activity and tendency to produce salivation can be determined or verified using the following methods:

Compounds can be tested using the following A9 L-ml assay-Stimulation of phosphoinositol hydrolysis in A9 L-ml cells:

A9-L-ml cells were cultured to confluence in 75 mL flasks containing Dubecco's modified essential media. Cells were prelabeled with 1 μCi/mL of myo[2–3 H]inositol (Amersham Inc, 16.3 Ci/mmol) for 48 h prior to assay. On the day of assay, cells were detached using a 30 s exposure to 0.25% trypsin in 1 mM EDTA. The cells were collected by centrifugation (300×g for 5 min) and resuspended in oxygenated HEPES buffer containing 10 mM LiCl, 142 mM NaCl, 5.6 mM KCl, 2.2 mM $CaCl_2$, 1 mM $MgCl_2$, 3.6 mM $NaHCO_3$, 5.6 mM D-glucose, and 30 mM sodium HEPES at pH 7.4. Cells were incubated at 37 C. for 45 min in the presence of varying concentrations of drug. The reaction was terminated by the addition of 3 mL of ice cold 10 mM LiCl, sonicated, and centrifugated at 20,000×g. The supernatent was decanted over a Accell QMA anion exchange SEP-PAK cartridge in the formate form (Waters Associates, Milford, Mass.). The cartridges were washed with 10 mL of $H_2O$ followed by 10 mL of 5 mM sodium borate. [3 H]PI was eluted directly into scintillation vials for counting with 4 mL of 0.1 ammonium formate/0.01 mM formic acid/5 mM sodium borate. Data is expressed as the percent of total,[3 H]PI stimulated in the presence of 1 mM carbachol. Half-maximal values (EC50) were determined from the mean of seven point curves using a four parameter logistic model.

Salivation in mice:

Mice weighing 20 to 30 g were used for salivation testing. Mice, in groups of five, were injected i.p. with 10 mg/kg doses of compound dissolved in distilled water. After, 30 min, salivation and tremor were scored on a scale of 0, 1, or 2, where 0=no effect, 1=moderate salivation or tremor, and 2=marked salivation or tremor. Those compounds producing an average score of 1 were tested at half log lower doses until a score lower than 1 was achieved. The lowest dose of compound producing a score of 1 was expressed at the minimum effective dose (MED).

The compounds of the invention are effective over a wide dosage range. For example, in the treatment of adult humans, dosages from about 0.05 to about 100 mg, preferably from about 0.1 to about 100 mg, per day may be used. A most preferable dosage is about 0.1 mg to about 70 mg per day. In choosing a regimen for patients suffering from diseases in the central nervous system caused by malfunctioning of the muscarinic cholinergic system it may frequently be necessary to begin with a dosage of from about 20 to about 70 mg per day and when the condition is under control to reduce the dosage as low as from about 0.1 to about 10 mg per day. The exact dosage will depend upon the mode of administration, form in which administered, the subject to be treated and the body weight of the subject to be treated, and the preference and experience of the physician or prescribing caregiver in charge.

The route of administration may be any route, which effectively transports the active compound to the appropriate or desired site of action, such as oral or parenteral e.g. rectal, transdermal, depot, subcutaneous, intravenous, intramuscular or intranasal, the oral route being preferred.

Typical compositions include a compound of formula I or a pharmaceutically acceptable acid addition salt thereof, associated with a pharmaceutically acceptable excipient which may be a carrier, or a diluent or be diluted by a carrier, or enclosed within a carrier which can be in the form of a capsule, sachet, paper, or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose and polyvinylpyrrolidone. The formulations may also include wetting agents, emulsifying and suspending agents, preserving agents, sweetening agents, or flavoring agents. The formulations of the invention may be formulated so as to provide quick, sustained, or delayed release of the active ingredient after administration to the patient by employing procedures well known in the art.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

Generally, the compounds are dispensed in unit form comprising from about 0.1 to about 100 mg in a pharmaceutically acceptable carrier per unit dosage.

The compounds of this invention may be suitable for administration to an animal. Such animals include both domestic animals, for example livestock, laboratory animals, and household pets, and non-domestic animals such as wildlife. More preferredly, the animal is a vertebrate. Most preferredly, a compound of this invention shall be administered to a mammal. It is especially preferred that the animal is a domestic mammal or a human. The most preferred mammal is a human. For such purposes, a compound of this invention may be administered as a feed additive.

In order to more fully illustrate the operation of this invention, the following formulation examples are provided. The examples are illustrative only, and are not intended to limit the scope of the invention in any way.

FORMULATION 1

| A typical tablet, appropriate for use in this method, may be prepared using conventional techniques and may contain: | | |
| --- | --- | --- |
| (%) | Amount per Tablet | Concentration by Weight |
| a compound of this invention | 5.0 mg | 4.7 |
| Lactosum | 67.8 mg Ph. Eur. | 64.2 |
| Avicel ® | 31.4 mg | 29.8 |
| Amberlite ® | 1.0 mg | 1.0 |
| magnesium stearate | 0.25 mg | 0.3 |
| | 105.45 mg | 100 |

FORMULATION 2

| Hard gelatin capsules are prepared using the following ingredients: | | |
| --- | --- | --- |
| (%) | Amount per Tablet | Concentration by Weight |
| a compound of this invention | 0.1 mg | 0.05 |

FORMULATION 2-continued

| Hard gelatin capsules are prepared using the following ingredients: | | |
| --- | --- | --- |
| (%) | Amount per Tablet | Concentration by Weight |
| starch dried | 200 mg | 95.2 |
| magnesium stearate | 10 mg | 4.8 |
| | 210.1 mg | 100 |

The above ingredients are mixed and filled into hard gelatin capsules in 210.1 mg quantities.

FORMULATION 3

| Suspensions each containing 1 mg of medicament per 5 mL dose are as follows: | |
| --- | --- |
| | Amount per 5 mL of suspension |
| a compound of this invention | 1 mg |
| sodium carboxymethyl cellulose | 50 mg |
| syrup | 1.25 mL |
| benzoic acid solution | 0.10 mL |
| flavor | q.v. |
| color | q.v. |
| water | q.s. to 5 mL |

The medicament is passed through a No. 45 mesh U.S. sieve and mixed with the sodium carboxymethyl cellulose and syrup to form a smooth paste. The benzoic acid solution, flavor and color is diluted with some of the water and added to the paste with stirring. Sufficient water is then added to produce the required volume.

The intermediates and processes of the present invention are useful for preparing compounds having beneficial muscarinic receptor activity. The compounds of the present invention have such useful muscarinic receptor activity. Certain compounds and conditions within the scope of this invention are preferred. The following conditions, invention embodiments, and compound characteristics listed in tabular form may be independently combined to produce a variety of preferred compounds and process conditions. The following list of embodiments of this invention is not intended to limit the scope of this invention in any way.

Some prefered characteristics of compounds of formula I are:

A) $R^9$ is chloro and $R^8$ is hydrogen;
B) $R^9$ is chloro and in the para position;
C) the Formula I compound is endo;
D) $R^8$ is ethyl or isopropyl;
E) $R^9$ is methoxy;
F) W is O;
G) W is S;
H) a compound of the formula II

II

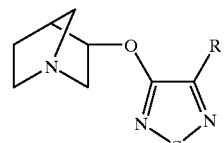

wherein R is selected from the group consisting of:

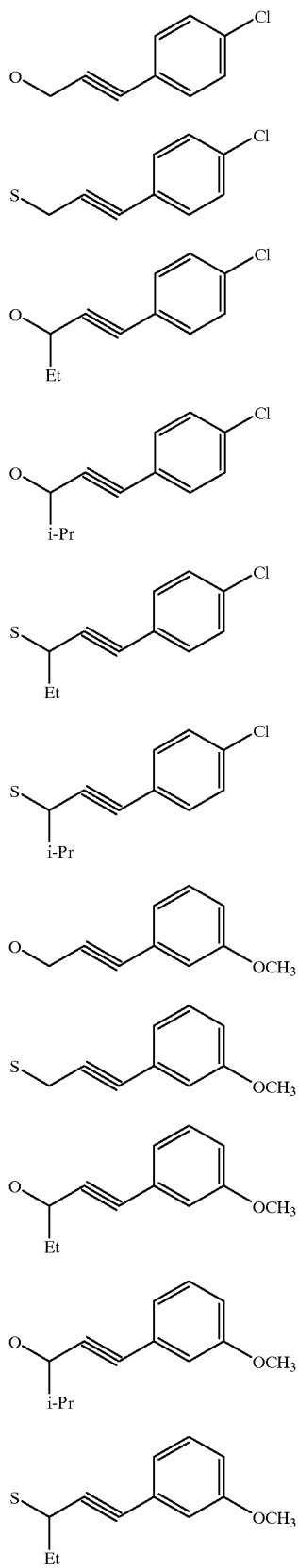

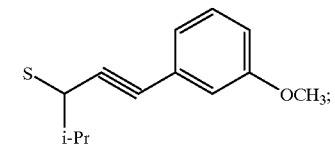

I) A compound having a side chain named in letter H above herein, wherein W is an oxygen group.

J) a compound wherein $R^8$ is ethyl and $R^9$ is fluoro and $R^9$ is located in the para position.

To further clarify, the invention, the following compounds are examples of compounds which are envisioned by the present invention. The following examples are merely illustrative and are not intended to limit the scope of the present invention in any way. Exo-3-(3-[3-phenyl-2-propynyl-1-oxy]-1,2,5-thiadiazol-4-yloxy)-1-azabicyclo[2.2.1]heptane, Exo-3-(3-[3-(3-methoxyphenyl )-2-propynyl-1-oxy]-1,2,5-thiadiazol-4-yloxy)-1-azabicyclo[2.2.1]heptane, Exo-3-(3-[3-(3-ethoxyphenyl)-2-propynyl-1-oxy]-1,2,5-thiadiazol-4-yloxy)-1-azabicyclo[2.2.1]heptane, 3-(3-[3-(3-butoxyphenyl )-2-propynyl-1-oxy]-1,2,5-thiadiazol-4-yloxy)-1-azabicyclo[2.2.1]heptane, 3-(3-[3-(3-trifluoromethylphenyl)-2-propynyl-1-oxy]-1,2,5-thiadiazol-4-yloxy)-1-azabicyclo[2.2.1]heptane, 3-(3-[3-(2-trifluoromethylphenyl)-2-propynyl-1-oxy]-1,2,5-thiadiazol-4-yloxy)-1-azabicyclo[2.2.1]heptane, 3-(3-[3-(4-trifluoromethylphenyl)-2-propynyl-1-oxy]-1,2,5-thiadiazol-4-yloxy)-1-azabicyclo[2.2.1]heptane, 3-(3-[3-(3-methylphenyl)-2-propynyl-1-oxy]-1,2,5-thiadiazol-4-yloxy)-1-azabicyclo[2.2.1]heptane, 3-(3-[3-(3-tert-butylphenyl)-2-propynyl-1-oxy]-1,2,5-thiadiazol-4-yloxy)-1-azabicyclo[2.2.1]heptane, 3-(3-[3-(2-chlorophenyl)-2-propynyl-1-oxy]-1,2,5-thiadiazol-4-yloxy)-1-azabicyclo [2.2.1]heptane, 3-(3-[3-(3-fluorophenyl)-2-propynyl-1-oxy]-1,2,5-thiadiazol-4-yloxy)-1-azabicyclo [2.2.1]heptane, 3-(3-[3-(3-trifluromethoxyphenyl)-2-propynyl-1-oxy]-1,2,5-thiadiazol-4-yloxy)-1-azabicyclo[2.2.1]heptane, and 3-(3-[3-(4-trifluoromethoxyphenyl)-2-propynyl-1-oxy]-1,2,5-thiadiazol-4-yloxy)-1-azabicyclo[2.2.1]heptane.

The invention will now be described in further detail with reference to the following examples. The examples are provided for illustrative purposes, and are not to be construed as limiting the scope of the invention in any way.

PREPARATION 1

3-Chloro-4-(1-butylthio)-1,2,5-thiadiazole

Cyanogen (36 g, 0.69 mol) was bubbled into ether (250 mL) maintained at −10° C. To the solution was added dropwise diethylamine (3 mL) followed by dropwise addition of 1-butylthiol (47 mL, 0.64 mol) at such a rate that the temperature did not exceed −5° C. The reaction was maintained below 0° C. for 5 h then stirred at ambient overnight. Ether was distilled from the reaction until the pot temperature reached 50° C. The reaction was cooled to ambient and then added dropwise to a solution of sulfur monochloride (55 mL, 0.688 mol) in DMF (50 mL) that was cooled to 5° C. Cooling was removed and reaction was stirred overnight. The reaction was cooled in an ice-water bath and excess sulfur monochloride destroyed by careful addition of $H_2O$ while maintaining the temperature below 40° C. The liquid was decanted from the semi-solid sulfur precipitant and the sulfur residue triturated with hexane. The aqueous fraction was extracted with hexane (3 X) and the combined extracts and triturants were washed with $H_2O$, aqueous $NaHCO_3$, brine, dried, and the solvent evaporated. The residue was distilled at 2 mm Hg to give a yellow liquid (24.6 g), b.p. 105–110° C. (Compound 1).

PREPARATION 2

3-Butylthio-4-hydroxy-1,2,5-thiadiazole

A solution of Compound 1 (20.9 g), DMSO (20 mL) and 2 N NaOH (205 mL) was headed to reflux overnight. The solution was cooled to 15° C. and concentrated HCl was added until the pH was 1. The solid was collected, washed with water, and dried to give a solid (17.68 g). Recrystallization from heptane gave white crystals, m.p. 72–72.5° C. (Compound 300).

PREPARATION 3

(±)Exo-3-Butylthio-4-(1-azabicyclo[2.2.1]heptyl-3-oxy)-1, 2,5-thiadiazole

A solution of triphenylphosphine (0.7 g) and Compound 300 (0.5 g) in THF (20 mL) was cooled in ice-water. Diethyl diazodicarboxylate (0.4 mL) was added dropwise followed by addition of (±)endo-3-hydroxy-1-azabicyclo [2.2.1] heptane (0.29 g). Cooling was removed and after 1 h the solvent was evaporated. The residue was suspended in cold water, acidified, and extracted with ether. The aqueous fraction was made basic and extracted with EtOAc. The extracts were dried, the solvent evaporated, and the residue purified by radial chromatography eluting with 5%-EtOH-0.5% $NH_4OH$—$CHCl_3$ to give a clear oil. The HCl salt crystallized from EtOAc as white crystals (0.44 g), m.p. 147–148° C. (Compound 301).

PREPARATION 4

3-Propylthio-4-hydroxy-1,2,5-thiadiazole

A mixture of 3-chloro-4-propylthio-1,2,5-thiadiazole (10 g), 2 N NaOH (100 mL), and DMSO (10 mL) was heated to reflux for 24 h. The solution was cooled and extracted with ether. The aqueous fraction was acidified with conc. HCl and cooled in ice-water for 3 h. The resulting solid was collected, washed with a small amount of cold water to give a white solid (8.15 g). Recrystallization from heptane gave white crystals, m.p. 84–85° C.

PREPARATION 5

(±) Exo-3-Propylthio-4-(1-azabicyclo[2.2.1]heptyl-3-oxy)-1, 2,5-thiadiazole

A solution of triphenylphosphine (3.96 g) and 3-propylthio-4-hydroxy-1,2,5-thiadiazole (2.62 g) in THF (110 mL) was cooled in ice-water. Diethyl diazodicarboxylate (2.27 mL) was added dropwise followed by addition of (+)endo-3-hydroxy-1-azabicyclo [2.2.1]heptane (1.64 g). Cooling was removed and after 23 h the solvent was evaporated. The residue was suspended in cold water, acidified, and extracted with ether. The aqueous fraction was made basic and extracted with ether. The extracts were dried, the solvent evaporated, and the residue purified by radial chromatography eluting with 5%-EtOH-0.5% $NH_4OH$—$CHCl_3$ to give a clear oil, 2.69 g. The HCl salt crystallized from $CHCl_3$-ether as white crystals, m.p. 176–177° C.

PREPARATION 6

(±)Exo-3-Propylsulfonyl-4-(1-azabicyclo[2.2.1]heptyl-3-oxy)-1,2,5-thiadiazole (±)Exo-3-Propylthio-4-(1-azabicyclo[2.2.1]heptyl-3-oxy)-1, 2,5-thiadiazole (2.0 g) was dissolved in a mixture of 1N HCl (9 mL) and $H_2O$ (15 mL) and cooled in ice-water. To the solution was added dropwise a solution of Oxone (6.94 g) in $H_2O$ (35 mL). Cooling was removed and the reaction stirred 5.5 h. Excess oxidant was destroyed with sodium bisulfite and the reaction again cooled in ice-water. The solution was made basic with 5 N NaOH and extracted with EtOAc to give a yellow oil (2.01 g).

EXAMPLE 1

(±) Exo-3- (3- (4-Chlorophenyl)propynyloxy-4- (1-azabicyclo [2.2.1]heptyl-3-oxy)-1, 2,5-thiadiazole A solution of 3-(4-chlorophenyl)propynol (0.25 g) in THF (15 mL) is cooled in ice-water as potassium tert-butoxide (0.17 g) is added. After about 10 min, (±)exo-3-propylsulfonyl-4-(1-azabicyclo[2.2.1]heptyl-3-oxy)-1,2,5-thiadiazole (0.2 g) is added and the reaction stirred 1 h. The reaction is quenched with 5 N HCl (1 mL) and the solvent evaporated. The residue is suspended in cold water and extracted. The aqueous solution is made basic and extracted. The extracts are dried, the solvent is evaporated, and the residue converted to a salt that is recrystallized.

EXAMPLE 2

Endo-3-(3-[3-(4-fluorophenyl)-2-propynyl-1-oxy]-1, 2,5-thiadiazol-4-yloxy)-1-azabicyclo[2.2.1]heptane, oxalate A suspension of sodium hydride (90 mg, 3.0 mmol) in dry THF (30 ml) and 3-(4-fluorophenyl)-2-propyn-1-ol (225 mg, 1.5 mmol) was stirred at room temperature for 1 h under nitrogen. The reaction was then cooled in ice-water and added endo-3-(3-propylsulfonyl-1,2,5-thiadiazol-4-yloxy)-1-azabicyclo[2.2.1]heptane (303 mg, 1.0 mmol). After 16 h the cold reaction was quenched with water and the product extracted with ether (3 x). The extracts were dried ($MgSO_4$) and the solvent evaporated. The product was taken up in acetone and precipitated with oxalic acid in acetone followed by ether to give 180 mg (41%) of the title compound. M.p. 163–165_C. Compound 4.

EXAMPLE 3

The following compound was made in substantially the same manner as described in example 2 by using the reagents indicated:
Endo-3-(3-[3-phenyl-2-propynyl-1-oxy]-1,2,5-thiadiazol-4-yloxy)-1-azabicyclo[2.2.1]heptane, oxalate from endo-3-(3-propylsulfonyl-1,2,5-thiadiazol-4-yloxy)-1-azabicyclo[2.2.1]heptane, oxalate and 3-phenyl-2-propyn-1-ol. Yield: 81%. M.p. 158–159_C. Compound 5.
Endo-3-(3-[3-(3-methoxyphenyl)-2-propynyl-1-oxy]-1,2,5-thiadiazol-4-yloxy)-1-azabicyclo[2.2.1]heptane, oxalate from endo-3-(3-propylsulfonyl-1,2,5-thiadiazol-4-yloxy)-1-azabicyclo[2.2.1]heptane, oxalate and 3-(3-methoxyphenyl)-2-propyn-1-ol. Yield: 47%. M.p. 142–143_C. Compound 6.
Endo-3-(3-[3-(4-chlorophenyl)-2-propynyl-1-oxy]-1,2,5-thiadiazol-4-yloxy)-1-azabicyclo[2.2.1]heptane, oxalate from endo-3-(3-propylsulfonyl-1,2,5-thiadiazol-4-yloxy)-1-azabicyclo[2.2.1]heptane, oxalate and 3-(4-chlorophenyl)-2-propyn-1-ol. Yield: 40%. M.p. 118–122_C. Compound 18.

Endo-3-(3-[1-(3-methoxyphenyl)-1-pentyn-3-yloxy]-1,2,5-thiadiazol-4-yloxy)-1-azabicyclo[2.2.1]heptane, oxalate from endo-3-(3-propylsulfonyl-1,2,5-thiadiazol-4-yloxy)-1-azabicyclo[2.2.1]heptane, oxalate and 1-(3-methoxyphenyl)-1-pentyn-3-ol. Yield: 25%. M.p. 98–101__ C. Compound 19.

Endo-3-(3-(3-(3-trifluoromethylphenyl)-2-propynyl-1-oxy)-1, 2,5-thiadiazol-4-yloxy)-1-azabicyclo[2.2.1]heptane, oxalate from endo-3-(3-propylsulfonyl-1,2,5-thiadiazol-4-yloxy)-1-azabicyclo[2.2.1]heptane, oxalate (example 5) and 3-(3-trifluoromethylphenyl)-2-propyn-1-ol. M.p. 131–135__ C. Compound 23.

Endo-3-(3-(3-(3-fluorophenyl)-2-propyn-1-yloxy)-1.2.5-thiadiazol-4-yloxy-1-azabicyclo[2.2.1]heptane, oxalate from endo-3-(3-propylsulfonyl-1,2,5-thiadiazol-4-yloxy)-1-azabicyclo[2.2.1]heptane, oxalate and 3-(3-fluorophenyl)-2-propyn-1-ol. M.p. __C. Compound 31.

We claim:

1. A compound of formula I

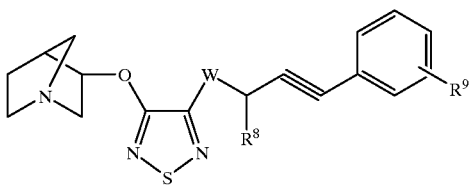

I

W is S or O;

$R^8$ is selected from the group consisting of hydrogen and $C_1$–$C_4$ alkyl;

$R^9$ is selected from the group consisting of halogen, $C_{1-4}$-alkyl, $C_{1-4}$-alkoxy, —CN, —OCF$_3$, —CF$_3$, —CONH$_2$ and —CSNH2; and pharmaceutically acceptable salts and solvates thereof.

2. A compound of claim 1 wherein $R^9$ is Cl.

3. A compound of claim 2 wherein $R^9$ is in the para position.

4. A compound of claim 3 wherein $R^8$ is hydrogen.

5. A compound of claim 4 wherein W is 0.

6. A compound of claim 1 wherein W is 0.

7. A compound of claim 1 wherein $R^9$ is OCH$_3$.

8. A compound of claim 7 wherein $R^8$ is ethyl.

9. A compound of claim 7 wherein $R^8$ is propyl.

10. A compound of claim 1 selected from the group consisting of (±)Exo-3-(3-(4-Chlorophenyl) propynyloxy-4-(1-azabicyclo[2.2.1]heptyl-3-oxy )-1,2,5-thiadiazole, Endo-3-(3-[3-(4-fluorophenyl)-2-propynyl-1-oxy]-1,2,5-thiadiazol-4-yloxy)-1-azabicyclo[2.2.1]heptane, Endo-3-(3-[3-(3-methoxyphenyl)-2-propynyl-1-oxy]-1,2,5-thiadiazol-4-yloxy)-1-azabicyclo [2.2.1]heptane, Endo-3-(3-[4-trifluoromethoxybenzyloxy ]-1,2,5-thiadiazol-4-yloxy)-1-azabicyclo [2.2.1]heptane, Endo-3-(3-[2-fluoro-4-(trifluoromethyl)-benzyloxy ]-1,2,5-thiadiazol-4-yloxy)-1-azabicyclo [2.2.1]heptane, Endo-3-(3-[3-(4-chlorophenyl)-2-propynyl-1-oxy]-1,2,5-thiadiazol-4-yloxy)-1-azabicyclo [2.2.1]heptane, Endo-3-(3-[1-(3-methoxyphenyl)-1-pentyn-3-yloxy]-1,2,5-thiadiazol-4-yloxy)-1-azabicyclo [2.2.1] heptane, Endo-3-(3-[1-(3-methoxyphenyl)-4-methyl-1-pentyn-3-yloxyl-1,2,5-thiadiazol-4-yloxy)-1-azabicyclo [2.2.1]heptane, Endo-3-(3-(3-(3-trifluoromethylphenyl)-2-propynyl-1-oxy)-1,2,5-thiadiazol-4-yloxy)-1-azabicyclo [2.2.1]heptane, Endo-(Z)-3-(3-(5-(4-fluorophenyl)-3-methyl-2-penten-4-yn-1-yloxy)-1, 2,5-thiadiazol-4-yloxy)-1-azabicyclo[2.2.1]heptane, Endo-(E)-3-(3-(5-(4-fluorophenyl)-3-methyl-2-penten-4-yn-1-yloxy)-1,2,5-thiadiazol-4-yloxy)-1-azabicyclo [2.2.1]heptane, Endo-(E/Z)-3-(3-(5-(4-fluorophenyl)-2-penten-4-yn-1-yloxy)-1,2,5-thiadiazol-4-yloxy)-1-azabicyclo[2.2.1]heptane, and Endo-3-(3-(3-(3-fluorophenyl)-2-propyn-1-yloxy)-1.2.5-thiadiazol-4-yloxy-1 -azabicyclo[2.2.1]heptane.

11. A compound of claim 10 wherein the compound is selected from the group consisting of (±)Exo-3-(3-(4-Chlorophenyl) propynyloxy-4-(1-azabicyclo[2.2.1]heptyl-3-oxy )-1,2,,5-thiadiazole, Endo-3-(3-[3-(4-fluorophenyl)-2-propynyl- 1-oxy]-1,2,5-thiadiazol-4-yloxy)-1-azabicyclo [2.2.1]heptane, Endo-3-(3-[4-(3-methoxyphenyl)-3 -butyn-2-yloxy]-1,2,5-thiadiazol-4-yloxy)-1-azabicyclo [2.2.1) heptane, Endo-3-(3-[3-(4-chlorophenyl)-2 -propynyl-1-oxy]-1,2,5-thiadiazol-4-yloxy)-1-azabicyclo [2.2.1]heptane, Endo-3-(3-[1-(3-methoxyphenyl)-1 -pentyn-3-yloxy]-1,2,5-thiadiazol-4-yloxy)-1-azabicyclo [2.2.1]heptane, Endo-3-(3-[1-(3-methoxyphenyl)-4-methyl-1-pentyn-3-yloxy]-1,2, 5-thiadiazol-4-yloxy)-1-azabicyclo [2.2.1]heptane, Endo-3-(3-(3-(3-trifluoromethylphenyl)-2-propynyl-1-oxy)-1,2,5-thiadiazol-4-yloxy)-1-azabicyclo[2.2.1)heptane, Endo-(Z)-3-(3-(5-(4-fluorophenyl)-3-methyl-2-penten-4-yn-1-yloxy)-1, 2,5-thiadiazol-4-yloxy)-1-azabicyclo[2.2.1] heptane, Endo-(E) -3- (3- (5- (-fluorophenyl)-3-methyl-2-penten-4-yn-1-yloxy)-1,2,5-thiadiazol-4-yloxy)-1-azabicyclo [2.2.1]heptane, Endo-(E/Z)-3-(3-(5-(4-fluorophenyl)-2-penten-4-yn-1-yloxy)-1,2,5-thiadiazol-4-yloxy )-1-azabicyclo[2.2.1]heptane, and Endo-3-(3-(3-fluorophenyl)-2-propyn-1-yloxy)-1.2.5-thiadiazol-4-yloxy-1 -azabicyclo[2.2.1]heptane.

12. A formulation comprising a compound of Formula I

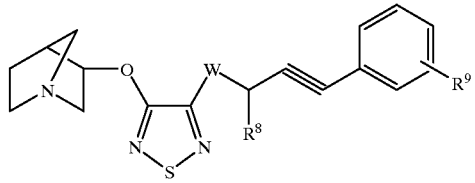

I

W is S or O;

$R^8$ is selected from the group consisting of hydrogen and $C_1$–$C_4$ alkyl;

$R^9$ is selected from the group consisting of halogen, —CN, $C_{1-4}$-alkyl, $C_{1-4}$-alkoxy, —OCF$_3$, —CF$_3$, —CONH$_2$ and —CSNH$_2$;

and one or more excipients, diluents, and/or carriers therefor.

13. A method for treating a condition which is mediated by a muscarinic receptor, comprising administering an effective amount of a compound of Formula I

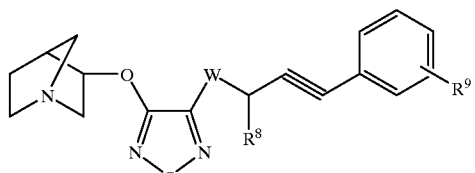

I

W is S or O;

$R^8$ is selected from the group consisting of hydrogen and $C_1$–$C_4$ alkyl;

$R^9$ is selected from the group consisting of halogen, —CN, $C_{1-4}$-alkyl, $C_{1-4}$-alkoxy, —$OCF_3$, —$CF_3$, —$CONH_2$ and —$CSNH_2$; to a patient in need thereof.

14. A method of claim 13 wherein the condition is selected from the group consisting of Alzheimer's disease, severely painful conditions, glaucoma, psychosis, anxiety, mania, bipolar disorder, schizophrenia or schizophreniform conditions, depression, sleeping disorders, epilepsy, cerebral ischemia, and gastrointestinal motility disorders.

15. A method of claim 14 wherein the condition is Alzheimer's disease.

16. A method of claim 14 wherein the condition is a psychosis.

* * * * *